United States Patent [19]

Wälischmiller

[11] Patent Number: 5,134,295

[45] Date of Patent: Jul. 28, 1992

[54] IRRADIATION APPARATUS

[76] Inventor: Hans Wälischmiller, Kapellenweg 5, D7778 Markdorf, Fed. Rep. of Germany

[21] Appl. No.: 677,586

[22] Filed: Mar. 29, 1991

[30] Foreign Application Priority Data

Apr. 19, 1990 [DE] Fed. Rep. of Germany ....... 4012398

[51] Int. Cl.⁵ .................................................. G21K 5/10
[52] U.S. Cl. ............................. 250/455.11; 250/497.1; 250/437; 250/436; 378/69; 378/68; 378/67; 378/66; 378/64
[58] Field of Search ............. 250/455.1, 497.1, 436 R, 250/437; 378/69, 68, 67, 66, 64

[56] References Cited

U.S. PATENT DOCUMENTS 2,968,734  1/1961  Yeomans ............................ 378/67
3,566,113  2/1971  Balanca et al. .................. 250/497.1
4,621,195  11/1986  Larsson ............................ 250/437

Primary Examiner—Jack I. Berman
Attorney, Agent, or Firm—Robert W. Becker & Associates

[57] ABSTRACT

An apparatus for irradiating a substance or object is provided. The apparatus has a source of radiation that is placed in a housing, one side of which is provided with a centrally disposed receiving chamber for the source of radiation, and the other side of which is provided with an irradiation chamber for receiving a receptacle that contains the medium that is to be irradiated, with the irradiation chamber being aligned with the receiving chamber. Disposed between the receiving chamber and the irradiation chamber is a valve provided with a through-bore for the source of radiation, which can be introduced into the irradiation chamber. The valve can be arrested in various angular positions. The irradiation chamber can be closed off by a removable plug.

19 Claims, 4 Drawing Sheets

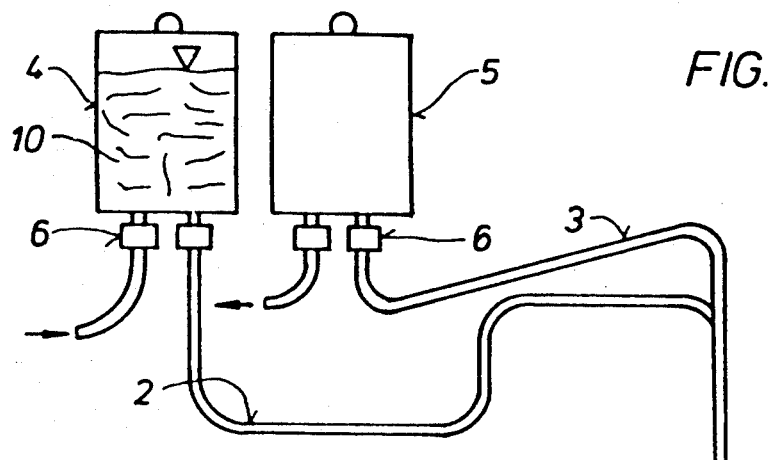
FIG. 6
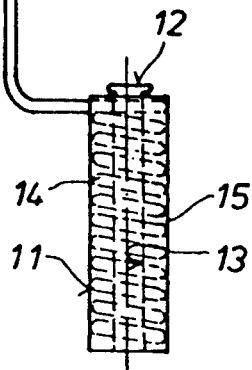
FIG. 7
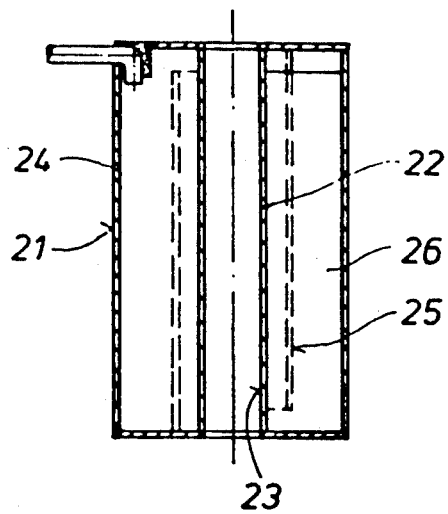
FIG. 8
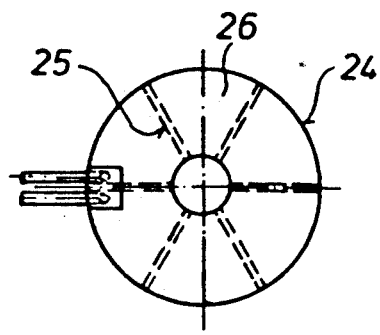

IRRADIATION APPARATUS

BACKGROUND OF THE INVENTION

The present invention relates to an apparatus for irradiating a substance, especially a liquid or gaseous medium, for example blood, in a receptacle via a source of radiation for ionizing rays, with this source of radiation being placed into a housing that can be blocked off, where the source of radiation acts upon the medium that is to be irradiated.

With one known irradiation apparatus of this general type, the housing that accommodates the source of radiation is provided on the side with an open recess in which a portion of the housing that is provided with a irradiation chamber is rotatably mounted The substance or object that is to be irradiated, such as a bottle, is inserted into this irradiation chamber and can be conveyed to the source of radiation by rotating the housing. Since the object can furthermore be rotated about its axis via a turntable that is provided in the irradiation chamber, it is possible to realize a uniform irradiation from the outside. However, despite the considerable structural expense that has been undertaken, a medium that is filled in a bottle or in a bag, and hence is at rest, can be respectively irradiated from only one side of the source of radiation. Furthermore, the time involved for moving the receptacle, and hence the medium that is to be irradiated, past the source of radiation is considerable; in addition, the rotational movement of the receptacle can have an unfavorable effect upon the medium that is to be irradiated. Consequently, the field of application of this known irradiation apparatus is limited, since it cannot be used in particular during operations, for example to irradiate the blood of a patient during an operation.

It is therefore an object of the present invention to provide an irradiation apparatus of the aforementioned general type via which it is possible not only to undertake an extremely intensive and safe irradiation of a medium, but also a flowing medium can flow by in the vicinity of the source of radiation, whereby the radiation dose that is to act upon the medium can be easily set in conformity with conditions, for example as a function of the flow velocity. Furthermore, provision of the irradiation apparatus should be undertaken without difficulty to provide for simple manipulation, yet it must be reliably insured that no rays can pass in an uncontrollable manner toward the outside, and that the irradiation apparatus can be operated in a logical manner and can function appropriately.

BRIEF DESCRIPTION OF THE DRAWINGS

These and other objects and advantages of the present invention will appear more clearly from the following specification in conjunction with the accompanying schematic drawings, in which:

FIG. 6 shows the receptacle provided for the apparatus of FIGS. 1 and 2 for receiving a liquid medium that is to be irradiated;

FIG. 7 is an axial cross-sectional view of a further embodiment of a receptacle for the inventive apparatus; and FIG. 8 i s a top view of the receptacle of FIG. 7.

SUMMARY OF THE INVENTION

Figure 1:
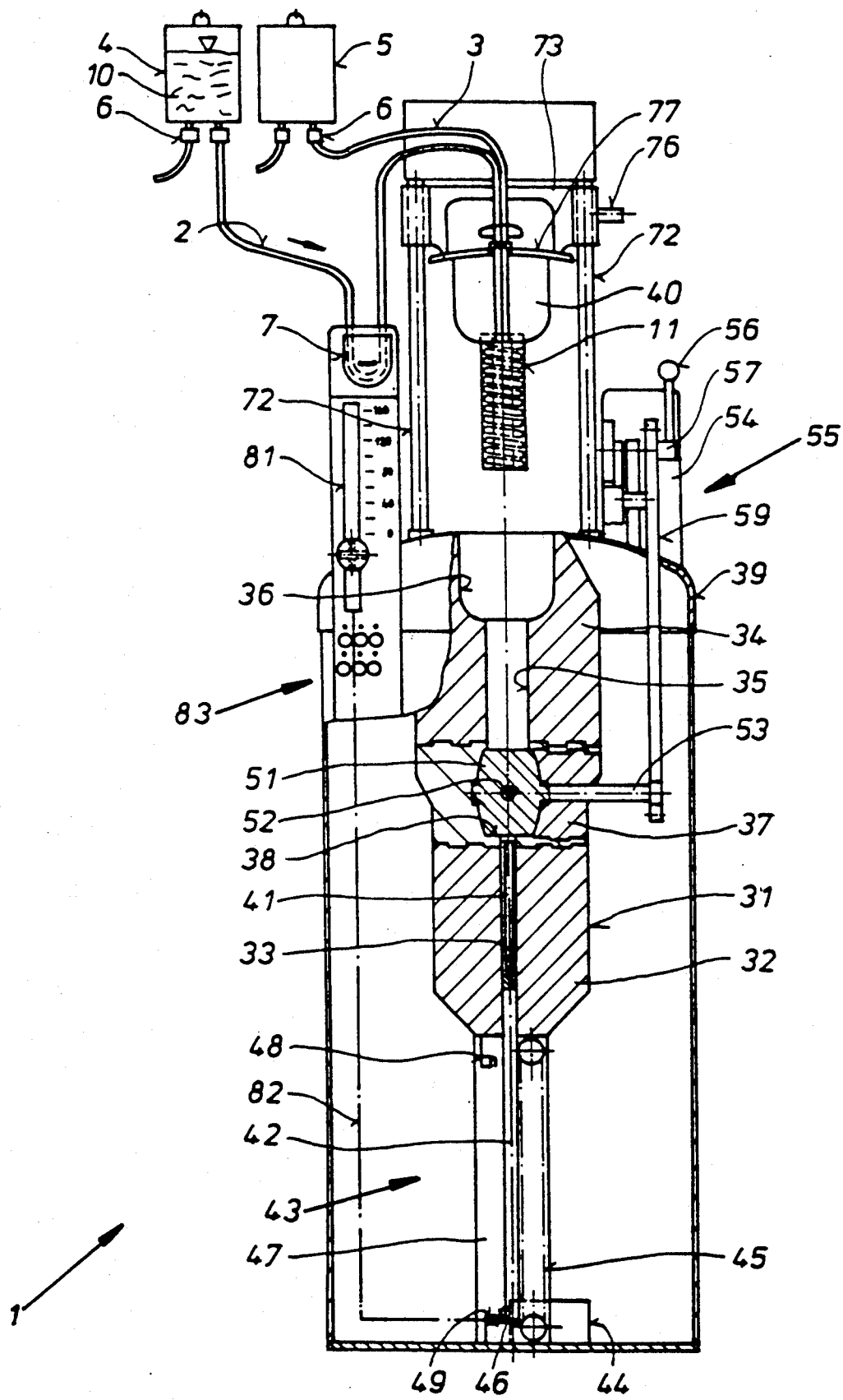
FIG. 1 is an axial cross-sectional view through one exemplary embodiment of the inventive irradiation apparatus during a provision process.

The irradiation apparatus of the present invention is characterized primarily in that one side of the housing, which preferably has a cylindrical or barrel shape, is provided with a centrally disposed receiving chamber for the source of radiation, and on the other side is provided with an irradiation chamber for receiving a receptacle that contains the medium that is to be irradiated, with the irradiation chamber being aligned with the receiving chamber, in that between the receiving chamber and the irradiation chamber a valve means is disposed that is mounted so as to be, for example, rotatable or slidable, and that is provided with a throughbore for the source of radiation, which can be introduced into the irradiation chamber, with the valve means being adapted to be arrested in various angular position thereof, and in that the irradiation chamber can be closed off by a removable plug means.

Expediently, the receptacle that receives the medium that is to be irradiated is provided with a centrally disposed opening means for receiving the source of radiation. This receptacle can be formed by tubing that is helically wound about a hollow core that receives the source of radiation. Alternatively, the receptacle could be formed by two spaced-apart tubes that are disposed one within the other, with the annular space formed between the tubes being divided by partitions into flow channels that communicate with one another. To ensure the transport of the medium through the receptacle, the latter should be connected to a pump mechanism, for example a hose pump that is mounted on the irradiation apparatus.

It is furthermore advantageous if the valve means is adapted to be shifted and is securable in three operating positions via a lever system.

In a straightforward manner, this lever system can comprise a pivotably mounted control lever that is disposed outside the housing, a shift lever that is mounted on the valve means, and a connector lever linked to these two levers: a locking member that is releasable as a function of the operating position of the plug means should be associated with the control lever.

It is furthermore expedient to introduce the source of radiation into the irradiation chamber of the housing via a preferably motor-driven lifting mechanism, and to vertically shift the plug means with the aid of bridge means, again via a motor, on a support structure that comprises two guide rail means.

It is also suitable to provide the bridge means with a shift pin via which the locking member of the lever system associated with the valve means is releasable, and to detachably secure the receptacle that receives the medium that is to be irritated to the plug means, for example via a stepped screw.

The plug means should furthermore be capable of being placed into a wider receiving opening that is formed in the housing and is aligned with the irradiation chamber for the receptacle. The plug means should also be provided with a cover that extends over this receiving opening, and furthermore should preferably be provided in a rim region with a recess through which lines that are to be connected to the receptacle can be conveyed.

For production reasons, the housing should be comprised of a lower portion that receives the source of radiation, an intermediate portion for the rotatable mounting of the valve means, and an upper portion that receives the receptacle. The housing can furthermore be provided with a closed casing on which it is also possible to mount an indicator means that is mechanically connected directly to the source of radiation or to the lifting mechanism thereof.

With an irradiation apparatus constructed pursuant to the teaching of the present invention, it is possible without difficulty to extremely intensely expose the object or substance that is to be irradiated to the ionizing rays given off by the source of radiation, and nonetheless to be able to perform irradiation in a safe manner; above all, it is also possible to readily irradiate a flowing medium. In particular, if the housing of the irradiation apparatus is provided with a receiving means into which a specially constructed receptacle for receiving medium that is to be irradiated can be placed, and if the source of radiation is disposed in such a way that it can be introduced into the receptacle, with such introduction being realized in only a prescribed operating position of a valve means that is operated in a controlled manner, the rays from the source of radiation then act from the inside upon the medium, which surrounds the source of radiation. The intensity of the radiation is then utilized very efficiently, so that the irradiation time for the transfer of a given radiation dose is considerably shorter than is possible with the heretofore known apparatus.

No centrifugal forces, which could lead, among other things, to separation, act upon the medium that is to be irradiated with the inventive irradiation apparatus, since the receptacle that receives the medium is stationary during an irradiation process. Furthermore, the irradiation can be easily metered, possibly even via a computer program, for example as a function of the position of the source of radiation, the duration of irradiation, and/or the flow velocity of the medium. However, it would be particularly advantageous if the medium could flow through the receptacle during an irradiation process, so that the irradiation apparatus could also be connected directly to a patient and/or could be utilized during an operation. The simple handling and the high operational reliability ensure that use of the inventive irradiation apparatus is always safe not only for operating personnel but also for a patient. Since the receptacle and its feed lines can be rapidly replaced and kept sterile, and especially since the irradiation time is short, a high degree of utilization results. The placement of a valve means that is to be opened only when the irradiation chamber is blocked off between this irradiation chamber and the receiving chamber for the source of radiation furthermore ensures that an uncontrolled irradiation and danger to personnel are precluded.

Further specific features of the present invention will be described in detail subsequently.

Description of Preferred Embodiments

Figure 2:
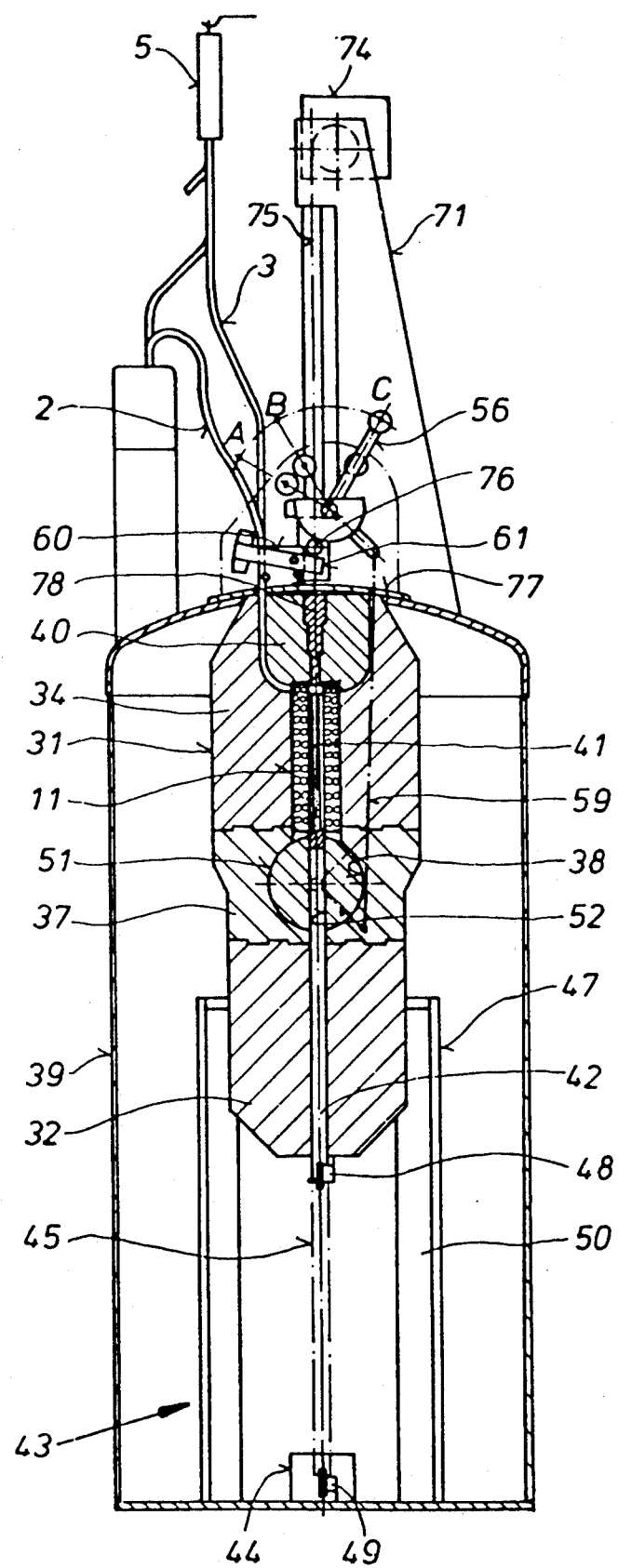
FIG. 2 i s a side view of the apparatus of FIG. 1 during irradiation.

Referring now to the drawings in detail, the apparatus 1 illustrated in FIGS. 1 and 2 serves for the irradiation of an object or substance, for example a liquid 10, with ionizing rays; the liquid 10, or some other gaseous or liquid fluid, can flow via the feed line 2 to a receptacle 11, which can be placed into the apparatus 1. A cylindrical or barrel-shaped housing 31 is provided with a receiving chamber 33 for a source of radiation 41, and is also provided with an irradiation chamber 35 into which the source of radiation 41 can be introduced. Disposed between the receiving chamber 33 and the irradiation chamber 35 is a valve means 51 that is adjustably controlled by a lever system 55; when the apparatus 1 is being loaded, as illustrated in FIG. 1, the valve means 51 serves to block off the receiving chamber 33 of the source of radiation 41.

As shown in greater detail in FIG. 6, the receptacle 11 for receiving the liquid 10 that is to be irradiated comprises a tubing 14, which is helically wound upon a hollow core 12, and a casing 15, so that an opening means 13 is formed into which the source of radiation 41 can be introduced. However, for example in conformity with the alternative construction illustrated in FIGS. 7 and 8, it would also be possible to provide a receptacle 21 that comprises an inner tube 22 and an outer tube 24 that is spaced from the inner tube 22, with partitions 25 being disposed between the inner and outer tubes in such a way that flow channels 26 are formed that communicate with one another. With this embodiment, during an irradiation process the source of radiation 41 can be introduced into the opening 23 of the inner tube 22.

Via the feed line 2, as well as a return line 3, the receptacle 11 or 21 can be connected directly to a patient, for example in order to irradiate the patient's blood; however, it is also possible to connect bags of blood 4 and 5 to the lines 2 and 3, which are equipped with shutoff valves 6; the liquid 10 that is to be irradiated is temporarily stored in these bags 4, 5. By means of a hose pump 7 that is mounted on the irradiation apparatus 1, the liquid 10 that is to be irradiated is continuously supplied to the receptacle 11 or 21 during an irradiation process.

Figure 4:
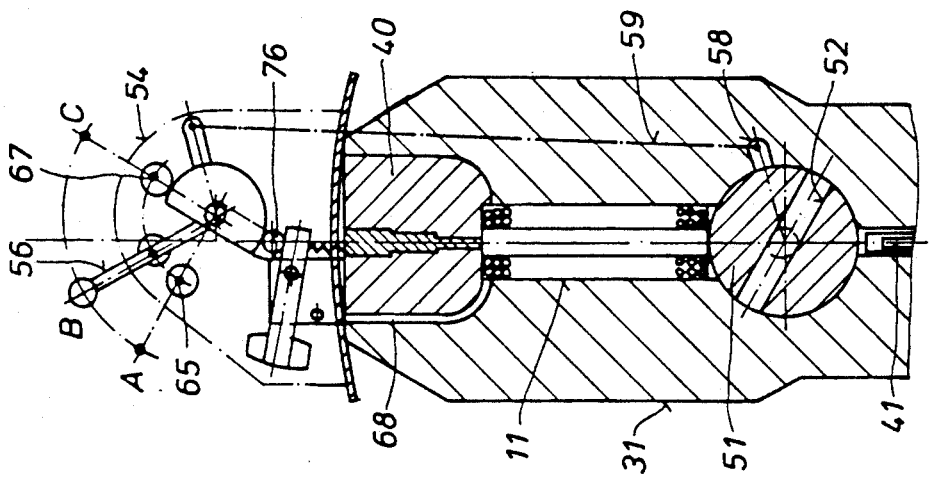

The housing 31 of the irradiation apparatus 1 is surrounded by a casing 39 and comprises a lower portion 32, in which the receiving chamber 33 for the source of radiation 41 is provided, an upper portion 34, in which the irradiation chamber 35 is provided, and an intermediate portion 37 in which, in a recess means 38 thereof, the valve means 51 is supported in such a way that it can slide or, in the illustrated embodiment, rotate. The upper portion 34 of the housing 31 is furthermore provided with a receiving opening 36 for a plug means 40 (FIGS. 2, 4 and 5); the receiving opening 36 is wider than the irradiation chamber 35. The housing 31 is held via support members 50.

To shift the source of radiation 41, which can be introduced into the irradiation chamber 35 and hence must be capable of being raised and lowered, a lifting mechanism 43 is provided that is supported on guide rail means 47. The lifting mechanism 43 is in the form of a chain drive 45 that can be driven by a motor 44; a plate 46 is mounted on the chain drive 45. The source of radiation 41 is disposed on a post or rod 42 that extends from the lower portion 32 of the housing 3 and rests upon the plate 46. The rod 42 also serves for blocking-off the receiving chamber 33. By turning the chain drive 45 in a clockwise direction, the source of radiation 41 can be raised; with an appropriate positioning of the valve means 51 the source of radiation 41 can be introduced entirely or partially into the irradiation chamber 35, depending upon the dosage rate required. Adjustment movements of the lifting mechanism 43 are monitored by limit switches 48 and 49.

So that in a particular position of the valve means 51, the source of radiation 41 can be introduced into the irradiation chamber 35, the valve means 51 is provided with a through-bore 52. Shifting of the valve means 51 is effected via the lever system 55, which acts upon a shaft 53 that is mounted on the valve means 51.

The lever system 55 comprises a control lever 56, which is rotatably mounted in a bracket 54 via a shaft 57, a shift lever 58 that is connected to the shaft 53 of the valve means 51, and a connector ever 59, which is linked to both the control lever 6 as well as to the shift lever 58. The control ever 56 is furthermore provided with a locking member 60 that cooperates with an abutment means 61 that can be shifted about a pin 62 against the force of a spring 63. The control lever 56 can be fixed in the positions A, B or C via a securing element 64 that is disposed on the control lever 56 and can be placed into recesses 65, 66 or 67 that are provided in the bracket 54.

Via a bridge means 73, the plug means 40 is held in a vertically adjustable manner on a support structure 71 that for this purpose is provided with two guide rail means 72. Secured to the bridge means 73 is a chain 75 that can be rolled up and can be moved with the aid of a motor 74. Also mounted on the bridge means 73 is a shift pin 76 that cooperates with the looking member 60 of the control lever 56. The receptacle 11 or 21 is removably secured to the plug means 40 via a stepped screw means 78. A cover 77 that extends over the receiving opening 36 is mounted on the plug means 40. In order for there to be enough space for the feed line 2 and the return line S to be conveyed out of the irradiation chamber 35 when the receptacle 11 or 21 is placed into the irradiation apparatus 1, the rim portion of the plug means 40 is provided with an appropriate recess 68.

Figure 3:
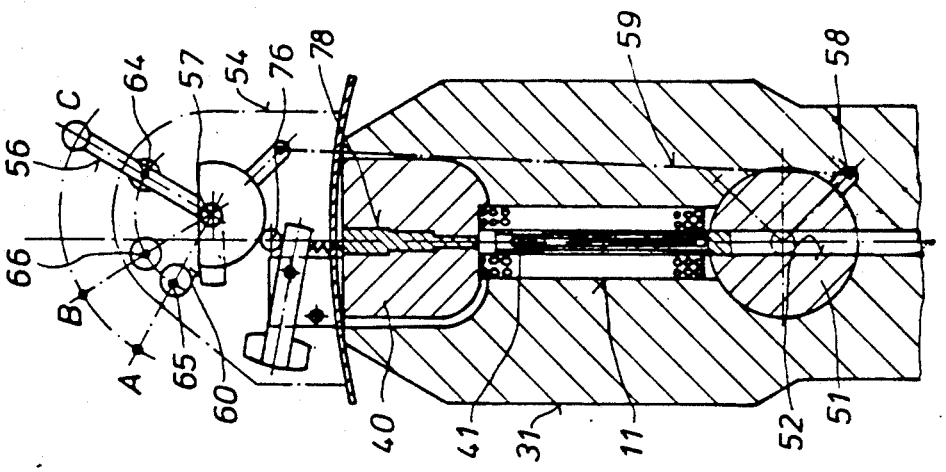
FIGS. 3-5 show various operating positions of the valve means of the irradiation apparatus of FIGS. 1 and 2, which valve means is controlled by a lever system.

If a receptacle 11 or 21 is to be placed into the irradiation apparatus 1, the plug means 40 is brought to the position shown in FIG. 1. However, before doing so, the valve means 51 should be turned in such a way as shown in FIG. 3) that the through-bore 52 thereof is not aligned with the receiving chamber 33, so that the source of radiation 41 disposed therein is blocked off. The locking member 60 that is disposed on the control lever 56 rests, in position A of the control lever 56, against the abutment means 61, thereby precluding an unintentional shifting of the valve means 51.

The receptacle 11 or 21 is then secured to the plug means 40, which is placed in the receiving opening 36. In so doing, the abutment means 61, via the shift pin 76 that is mounted on the bridge means 73, is shifted against the force of the spring 63, so that the control lever 56 can be shifted into the position B shown in FIG. 4. In this operating position, the receptacle 11 or 21 is already in the irradiation chamber 35, but the source of radiation 41 cannot yet be introduced into the irradiation chamber because the through-bore 52 of the valve means 51 is not yet aligned with the receiving chamber 33.

In this operating position, the irradiation apparatus 1 can be brought, for example, into an operating room, or the receptacle 11 or 21 can be connected to a patient, without an irradiation immediately being undertaken.

Figure 5:
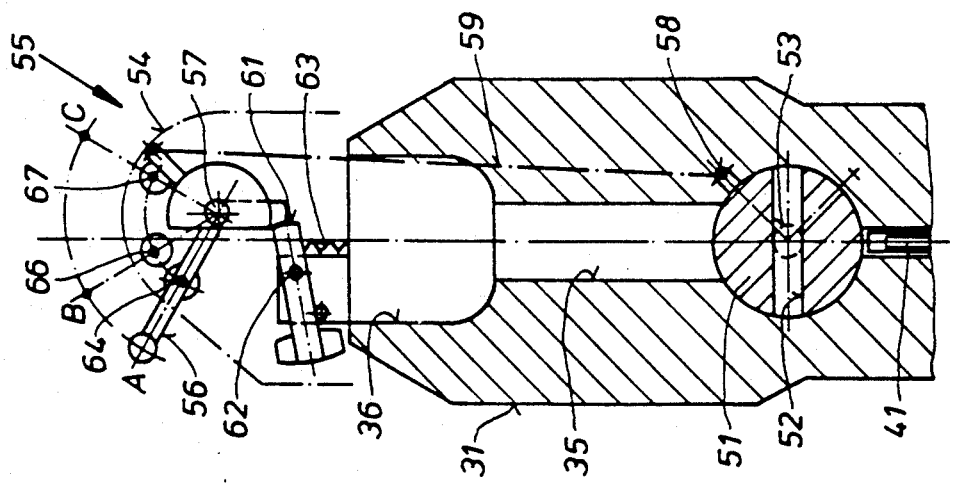

However, if the control lever 56 is rotated further into the position C, the valve means 51 is thereby shifted by the lever system 55 in such a way, as shown in FIG. 5, that the source of radiation 41 can, with the aid of the lifting mechanism 43, be introduced to a greater or lesser extent into the opening means 13 or 23 of the receptacle 11 or 21, and the medium that is disposed in or flows through this receptacle is irradiated. The radiation dose to which the medium 10 is exposed can be regulated as a function of the flow rate of the medium, the position of the source of radiation 41, and/or the duration of the irradiation.

To fix the control lever 56 in the position A, B or C and prevent an unintentional rotation thereof, a locking cylinder can be installed in the securing element 64. Furthermore, as indicated by a dot-dash line in FIG. 1, the source of radiation 41, or the lifting mechanism 43 associated therewith, can be mechanically connected via connecting means 82 to indicator means 81 mounted on the casing 39. In this way, it is possible to determine the position of the source of radiation at any time. In addition, it is possible to provide on the casing 39 control or indicator means 83, or a computer, via which it is possible to realize an automatic procedure or manipulation and/or to store irradiation values.

The present invention is, of course, in no way restricted to the specific disclosure of the specification and drawings, but also encompasses any modifications within the scope of the appended claims.

What I claim is:

1. An apparatus for irradiating a substance in a receptacle via a source of radiation for ionizing rays, comprising:
    a housing that on one side is provided with a centrally disposed receiving chamber for receiving said source of radiation, and on another side is provided with an irradiation chamber for receiving said receptacle that contains said substance that is to be irradiated, with said irradiation chamber being aligned with said receiving chamber;
    a valve means that is disposed in said housing between said receiving chamber and said irradiation chamber, with said valve means being provided with a through-bore;
    means for moving said valve means in such a way that said through-bore thereof is selectively in and out of alignment with said receiving and irradiation chambers;
    means for arresting said valve means in certain positions thereof;
    means for introducing said source of radiation through said through-bore of said valve means and into said irradiation chamber, where said source of radiation acts upon said substance; and
    removable plug means for closing off said irradiation chamber, said receptacle being connected to said plug means and having a centrally disposed opening for receiving said source of irradiation.

2. An apparatus according to claim 1, in which said receptacle comprises a hollow core, which forms said opening means for receiving said source of radiation, and also comprises tubing that is helically wound about said hollow core.

3. An apparatus according to claim 1, in which said receptacle comprises two tubes that are disposed one within the other and are spaced apart to form an annular chamber that is subdivided by partition means to form intercommunicating flow channels.

4. An apparatus according to claim 1, which includes pump means connected to said receptacle.

5. An apparatus according to claim 1, in which said means for moving said valve means comprises a lever system for moving and arresting said valve means in three operating positions.

6. An apparatus according to claim 5, in which said lever system comprises a control lever that is pivotably mounted outside said housing, a shift lever that is mounted on said valve means, and a connector lever that is linked to both said control lever and said shift lever.

7. An apparatus according to claim 6, which includes a looking member that is associated with said control lever and is releasable as a function of an operating position of said plug means.

8. An apparatus according to claim 1, in which said means for introducing said source of radiation into said irradiation chamber is a lifting mechanism.

9. An apparatus according to claim 6, which includes: a support structure comprised of two guide rail means, bridge means guided on said rail means and supporting said plug means, and a motor for shifting said bridge means and hence said plug means.

10. An apparatus according to claim 9, in which said bridge means is provided with a shift pin for releasing said locking member of said control lever.

11. An apparatus according to claim 1, which includes stepped screw means for detachably connecting said receptacle to said plug means.

12. An apparatus according to claim 1, in which said housing includes a receiving opening for receiving said plug means, with said receiving opening being aligned with said irradiation chamber.

13. An apparatus according to claim 12, in which said plug means is provided with a cover that extends over said receiving opening.

14. An apparatus according to claim 1, in which said plug means is provided with a recess for receiving conveying lines that are to be connected to said receptacle.

15. An apparatus according to claim 1, in which said housing has a generally cylindrical configuration.

16. An apparatus according to claim 15, in which said housing comprises: a lower portion that contains said receiving chamber for said source of radiation, an intermediate portion for rotatably receiving said valve means, and an upper portion that contains said irradiation chamber for said receptacle.

17. An apparatus according to claim 15, in which said housing is provided with a closed casing.

18. An apparatus according to claim 17, which includes an indicator means that is mounted on said casing and is mechanically connected directly to one of said source of radiation and said means for introducing same into said irradiation chamber.

19. An apparatus according to claim 1, in which said receptacle is connected to said plug means in a detachable manner.

* * * * *